United States Patent [19]

Patz et al.

[11] Patent Number: 5,800,490

[45] Date of Patent: Sep. 1, 1998

[54] LIGHTWEIGHT PORTABLE COOLING OR HEATING DEVICE WITH MULTIPLE APPLICATIONS

[76] Inventors: Herbert Samuel Patz, 32 Harrison, Brookline, Mass. 02146-9658; Leslie Hugh Ross, 57 N. Warren Ave., Brockton, Mass. 02401-3425

[21] Appl. No.: 747,021

[22] Filed: Nov. 7, 1996

[51] Int. Cl.$^6$ .................................................. A61F 7/00
[52] U.S. Cl. .......................... 607/108; 607/112; 607/99; 607/114
[58] Field of Search .................... 607/104, 108–112, 607/114, 96–99; 165/46; 219/212; 126/204; 2/905

[56] References Cited

U.S. PATENT DOCUMENTS

| | | | |
|---|---|---|---|
| 4,470,263 | 9/1984 | Lehovec et al. | 62/3 |
| 4,483,021 | 11/1984 | McCall | 2/7 |
| 4,741,338 | 5/1988 | Miyame | 128/399 |
| 4,846,176 | 7/1989 | Golden | 607/104 |
| 4,860,748 | 8/1989 | Chiurco et al. | 128/399 |
| 5,169,384 | 12/1992 | Bosniak et al. | 607/108 X |
| 5,197,294 | 3/1993 | Galvan et al. | 62/3.62 |
| 5,365,739 | 11/1994 | Fetterly | 62/3.62 |

*Primary Examiner*—Jennifer Bahr
*Assistant Examiner*—Ryan Carter
*Attorney, Agent, or Firm*—Ronald R. Kilponen

[57] ABSTRACT

A modular device with an injury pack holder (10) is shown for providing cooling and/or heating therapy to an injury, having a generally tubular shape and open first end (15) and an open second end (16). A plurality of module openings (55a, 55b and 55c) are cut through the injury pack holder (10) and covered with a retention mesh (60). A thermoelectric assembly (75) containing a Peltier device (85), fan (110), radiator (120), first plate (80) and second plate (88), transfers heat energy to a gel pack (95) which cools or heats an area, is installed in one of the module openings (55a, 55b, 55c). A battery pack (99) can be installed in another module opening (55a, 55b, 55c) or can be remotely located for operation of the thermoelectric assembly (75). The thermoelectric assembly (75) can be operated with other power supply devices such as a household adapter (160) or an auto adapter (170). The injury pack holder (10) has a plurality of attachment straps (70a, 70b and 70c) for affixing the injury pack to various human and animal body parts and is user adjustable to provide various levels of compression and immobility to a body part or joint.

10 Claims, 12 Drawing Sheets

LIGHTWEIGHT PORTABLE COOLING OR HEATING DEVICE WITH MULTIPLE APPLICATIONS

FIELD OF INVENTION

This invention relates to a modular lightweight portable cooling and heating device. There are a number of important areas where a portable cooling and heating device can be applied. Examples of application areas include: therapeutic application for acute or chronic injury in humans or animals, a built in device for clothing to provide localized heat or cooling for thermal comfort, and lightweight cooling or heating source for portable containers used to maintain the temperature of food or other materials at a desired temperature.

BACKGROUND

The present version of the invention relates to an object for treating various injuries in humans and animals.

Various devices in the prior art have been developed which can treat injuries. None of the prior art has combined the features of the present invention to provide one product that treats many different types of injuries in various parts of a human or animal. It is difficult to treat various body parts because of the various configurations of both man and animal body parts. It is difficult to develop one device that can be used in many different ways, yet is practical.

This device utilizes a component or modular part approach in providing heating and cooling to various objects. It can also be used to provide heating or cooling to various objects or could be used to provide both heating and cooling. The first component is a mounting system. This system can be used on many different body shapes and sizes. The system can be used on various items of clothing or food containers that require heating or cooling.

The second component of this invention is the heating and/or cooling electronic device. This is a self contained electronic device that can provide either a heating and/or cooling energy. This device is of a relatively small size and can be encased to protect the individual components. The size makes it easy to mount the electronic device in a member or holder for cooling a human or animal part or alternatively mounted in a food cooler or lunch bag, or mountable in an article of clothing.

The third component is the power supply. This embodiment of the invention can use household current, a portable battery pack, automobile or other vehicle having a cigarette lighter or access to 12 V D.C. or other power sources such as solar in combination with the above.

The electronic device is designed to be versatile, portable and adaptable for use on many different types of items.

After injuries such as sprains and strains it is generally accepted that cooling to the injured ares is effective in the reduction of swelling which can cause additional localized damage. Other examples of injuries for which this device may be useful would include symptomatic relief from muscle aches and pains, arthritis, or carpal tunnel syndrome.

Many in the medical field recommend cooling of the injured area for a period of 24-48 hours after the injury to reduce swelling and edema. A commonly used acronym for injures is RICE (Fitness Theory and Practice, pp 141-142, Aerobic and Fitness Association of America, Sherman Oaks, Calif., Library of Congress Catalog Card No. 93-72944), which stands for Rest, Ice, Compression and Elevation.

Refer also to U.S. Pat. No. 4,860,748 and references therein for the therapeutic uses of cold and heat for injuries. Once this initial period has passed, heat is generally recommended to be applied to the area as this increases blood flow and thereby healing. Some professionals recommend a regime of alternating cooling and heating to aid healing of the injury.

Certain injuries may require the above or various combinations of the above stated features of the present version of the invention.

Once the area is immobilized it is generally accepted that either a cooling therapy, a heating therapy or both may be needed to diminish pain and promote healing. This would require the application of an additional object to the injured area. The prior art shows a number of devices, for example, cold therapy devices or cold packs which are mechanically struck to activate a chemical reaction. The cold lasts a limited time until the active chemical reagents are expended. An example of such a device is "Instant Cold Pack" manufactured by Baxter Healthcare Products, Catalog Number 11440-512. This product contains ammonium nitrate and water. Their disadvantages include the fact that they have a limited lifetime and for each subsequent use a new pack must be used making them uneconomical.

Another example of prior art for producing therapeutic heating and cooling is gel packs. One example is the "Hot N'Cold", "Hot Pack" and "Cold Pack"of Sunbeam-Oster household Products of Schaumburg, Ill., U.S. Pat. Nos. 4,920,964 and 1,301,579.

The above examples rely on cooling or heating an energy retaining material to a desired temperature and then applying the warmed or cooled energy retaining material to the injury. The length of time for which the energy retaining material is effective is limited by the heat capacity of the gel. This method cannot maintain the injured area at a specific comfortable temperature level for an extended period of time. The energy retaining material loses or gains heat energy to/from the surrounding environment until it achieves equilibrium with the surrounding environment or ambient temperature. Thus an undesirable feature of a gel pack, is that its temperature is continuously changing during use as it approaches the ambient temperature.

Furthermore, the initial temperature of a gel pack may be too extreme. For example, in an icing application, care must be taken to prevent frostbite; and for a heating application, care must be taken to prevent burns to skin and tissue. Typically a boundary layer is applied between the gel pack and skin to protect the skin from extreme temperatures. As the gel pack approaches the ambient temperature however, there is no need to protect the skin since the gel packs temperature is no longer extreme. Additionally, for maximum therapeutic efficiency, one should remove the boundary layer to help maintain the treated area at the appropriate temperature. This type of intervention during treatment is undesirable because one would prefer to be able to apply a temperature controlled pack or device and not have to worry with reconfiguring it during treatment.

To obtain a longer heating or cooling time period requires the use of a larger device or larger volume of energy retaining material. Thus if one requires a longer period of time for heating or cooling therapy, the device becomes large, bulky, and awkward to wear.

In addition, the gel type prior art cannot change from a cooling mode to a heating mode without changing the device attached to the body or area to be cooled or heated. With this prior art, you can obtain either a cooling therapy or a warming therapy, but not both without the inconvenient manipulation and changing of devices.

An alternative method to provide heating and cooling is with the use of Peltier devices. Examples of prior art include U.S. Pat. No. 4,741,338 (the '338 patent) and U.S. Pat. No. 4,860,748 (the '748 patent).

The '338 device utilizes multiple Peltier devices and fans, is not readily adjustable to multiple body parts, is expensive to manufacture and is not portable.

The '748 device utilizes multiple Peltier devices, is not readily adaptable to multiple body parts and places the Peltier devices directly on the skin.

Other prior art utilizes Peltier devices to cool clothing or other objects worn such as U.S. Pat. No. 5,197,294 (the '294 patent), U.S. Pat. No. 4,483,021 (the '021 patent) and U.S. Pat. No. 4,470,263 (the '263 patent). The '294 patent shows a cooling device connected to an umbilical cord and then to a suit worn by the user. The '021 shows a device mounted to a motorcycle helmet but does not include a cooling fan. The '263 patent shows no cooling fan and solar collectors as one energy source.

In addition to providing a constant temperature surface to an injured area, there are two additional important feature which the present invention provides. First, this invention provides compressive support to an injured area. Secondly, it is desirable in the case of an injured joint to reduce the mobility or range of motion of the joint. This embodiment of the invention has this feature. Thus the present version of the invention provides a self contained heating or cooling source capable of providing a constant temperature to an injured area and at the same time provides both compression and joint stabilization.

The present version of the invention can maintain a desirable temperature at the injury site for an extended period of time limited only by the power source. The present version of the invention utilizes a thermoelectric device and temperature sensing device to maintain the temperature of the energy retaining material until the power supply is depleted.

Once the power supply is depleted, the injured area is still maintained at the desired temperature until the energy retaining material achieves equilibrium with the surrounding environment. Provided the energy retaining material is pre-cooled, this version of the invention therefore uses both the thermoelectric device and the energy retaining material to keep the injury or body part at a user chosen temperature for a longer time period than the prior art.

The present version of the invention provides compressive support to body parts from the elastic nature of the device. This version of the device can be adjusted to fit many different body parts and sizes. The tightness of the device can be adjusted to a user defined level. This enables the device to fit animal or body parts of various sizes and provides the option of loosening or tightening the device with relative ease once it is affixed to an animal or human body part.

As far as understood, the prior art discussed does not teach or suggest the embodiments of the present invention.

SUMMARY

The present version of the invention is directed to a lightweight portable cooling or heating device with multiple applications.

A first object of the present invention is to provide a device that is portable.

Another object of the present invention is to provide a device that can be utilized in many different configurations on a human or animal body.

An additional object of the present version of the invention is to provide an easy method to provide compressive support to an injury or body part.

Another object of the present invention is to provide a device in which the tightness can be adjusted by the user with relative ease.

Another object of the present invention is to provide a device in which both the range of motion in a joint can be reduced and where the joint can be supported by providing compression to the body parts on either side of the joint.

Another object of the present invention is to provide a device to maintain a manually selected thermostatically controlled temperature to an injury or body part for an extended period of time limited only by the life of the power source.

An additional object of the present version of the invention is to provide a device that can be sterilized and utilized by more than one person or patient.

An additional object of the present version of the invention is to provide a device that provides the above features and is portable.

Another object of the present version of the invention is to provide a device that is thermostatically controlled in such a way to maximize the lifetime of the power source when the unit is being utilized in the portable mode.

An additional object of the present version of the invention is to provide a device that can be worn in public with minimum disruption to one's clothing and mobility except for the immobility expressly intended to support an injury.

An additional object of the present invention is to provide a modular device that can be utilized to heat or cool, such as lunch bags, storage containers and any other objects that may require localized heating or cooling.

These and other objects of the present version of the invention will be completely disclosed and described in the following specification, the accompanying drawings and the appended claims.

DETAILED DESCRIPTION

Referring now in greater detail to the drawings where like elements are indicated by like numerals there is shown an embodiment of the present invention, a Lightweight Portable Cooling or Heating Device with Multiple Applications, where the modular components are designed for human or animal injury treatment application.

Figure 1:
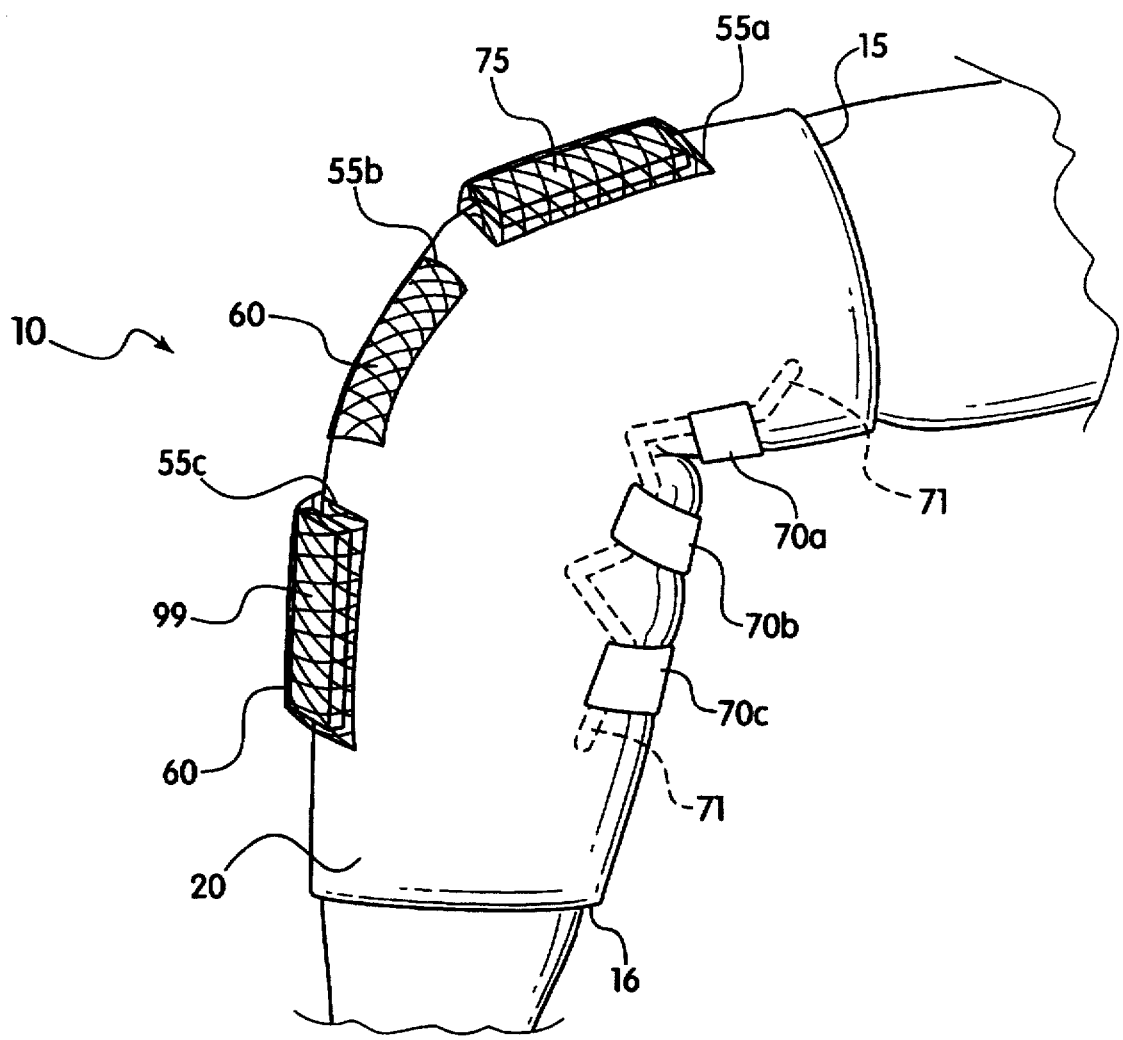
FIG. 1 shows a left side view of one embodiment of the device installed on a human leg.

A preferred embodiment of an injury pack holder 10 is primarily tubular in shape and manufactured from generally flexible materials. FIG. 1 shows the injury pack holder 10 left side view as it is affixed to a human leg. Affixing the injury pack holder 10 requires the user to insert a foot (not shown) into a first end 15 of the injury pack holder 10 and pull the injury pack holder 10 to the desired location, in this example, on the leg with the foot exiting a second end 16. In this embodiment, the first end 15 is slightly larger than the second end 16, giving the injury pack holder 10 a taper from the larger first end 15 to the smaller second end 16. This device, scaled in size, could also be used on many other body parts including but not limited to the ankle, thigh, calf, elbow, wrist and bicep.

Figure 2:
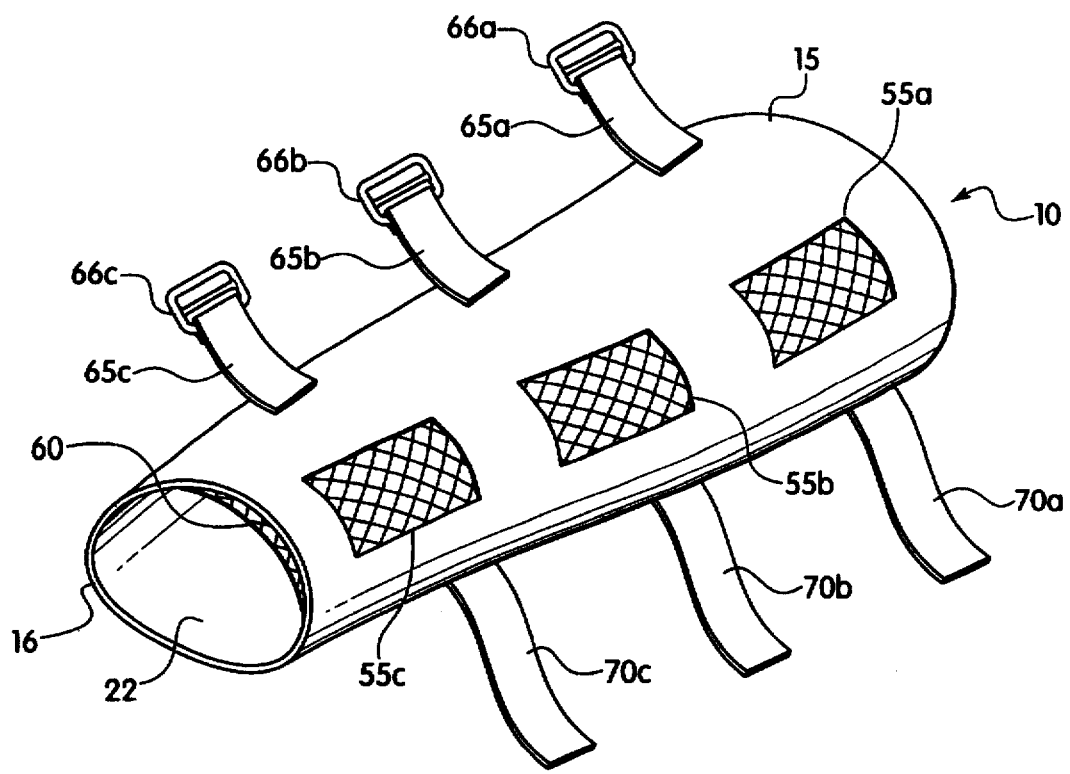
FIG. 2 hows one embodiment of the injury pack holder in an uninstalled position.
Figure 3:
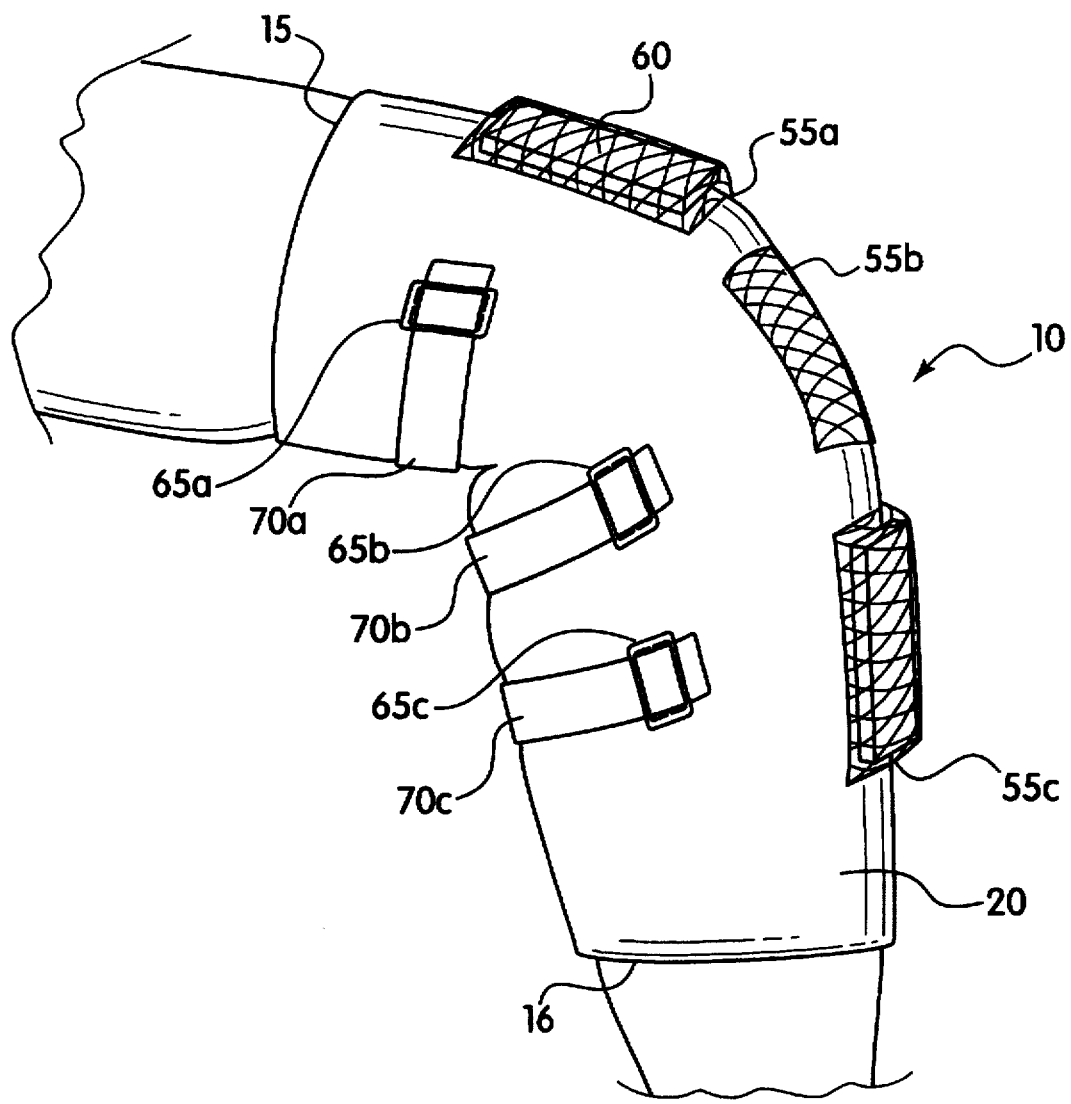
FIG. 3 shows a right side view of one embodiment of the portable cooling or heating device installed on a human leg.

The injury pack holder 10 is shown in a right side view installed on a human leg in FIG. 3 and in an uninstalled state in FIG. 2. An outer shell 20 is manufactured from a flexible material. The outer shell 20 can be manufactured from a variety of materials. One preferred embodiment is made by Griswold Rubber Company, Inc. of Moosup, Conn. model 18 #6122 having 2 way stretch poly on both sides. This material is similar to that used for scuba suits. Alternatively, the outer shell 20 can be made from Lycra or similar material or a combination of materials having similar properties.

An inner shell 22 tubular in design, FIG. 2, is positioned and sewn to the inside of the outer shell 20 and extends from the first end 15 to the second end 16. The inner shell 22 is sewn longitudinally on one seam (not shown) to the outer shell 20. The inner shell 22 is also sewn circumferentially to the outer shell 20 at the first end 15 and second end 16.

In this embodiment, a plurality of module openings 55a, 55b and 55c are rectangular holes cut through the outer shell 20 and the inner shell 22. This embodiment shows three module openings 55a, 55b and 55c. It is understood that more or less module openings could be utilized with the minimum number of module openings being one.

A retention mesh 60 is affixed to the inner shell 22 from the first end 15 to the second end 16 such that the retention mesh 60 creates a pocket in module openings 55a, 55b and 55c when objects are inserted into module openings 55a, 55b and 55c from the inside of the injury pack holder 10. Module openings 55a, 55b, and 55c can house a variety of objects such as traditional cooling packs (prior art) or in one embodiment a thermoelectric assembly 75, or various combinations of objects. The retention mesh 60 is sewn in two longitudinal seams running from the first end 15 to the second end 16 and at the first end 15 and second end 16 (not shown). The retention mesh in a preferred embodiment is manufactured by Versatex Co. of Foxboro, Mass., part number MA E03365 and is 30% lycra and 70% nylon.

A strap attachment 65a, FIG. 2., is affixed to the outer shell 20. An attachment strap 70a is affixed to the outer shell 20, FIG. 1. A strap attachment 65b is affixed to the outer shell 20. A strap attachment 65c is affixed to the outer shell 20. Strap attachments 65a, 65b and 65c are made from nylon webbing material looped and sewn as described.

Strap attachment 65a is looped through a strap loop 66a, likewise a strap loop 66b on strap attachment 65b and a strap loop 66c on strap attachment 65c. An attachment strap 70b is affixed to the outer shell 20.

An attachment strap 70c is affixed to the outer shell 20, FIG. 1. Attachment straps 70a, 70b and 70c are made from nylon webbing strapping. A reinforcement stitching 71 is sewn through the outer shell 20 and the inner shell in a "C" shaped pattern around each of the attachment straps 70a, 70b and 70c best shown in FIG. 1. Reinforcement stitching 71 helps retain the attachment straps 70a, 70b and 70c when they are tightened around a body or animal part, FIG. 3.

Figure 6:
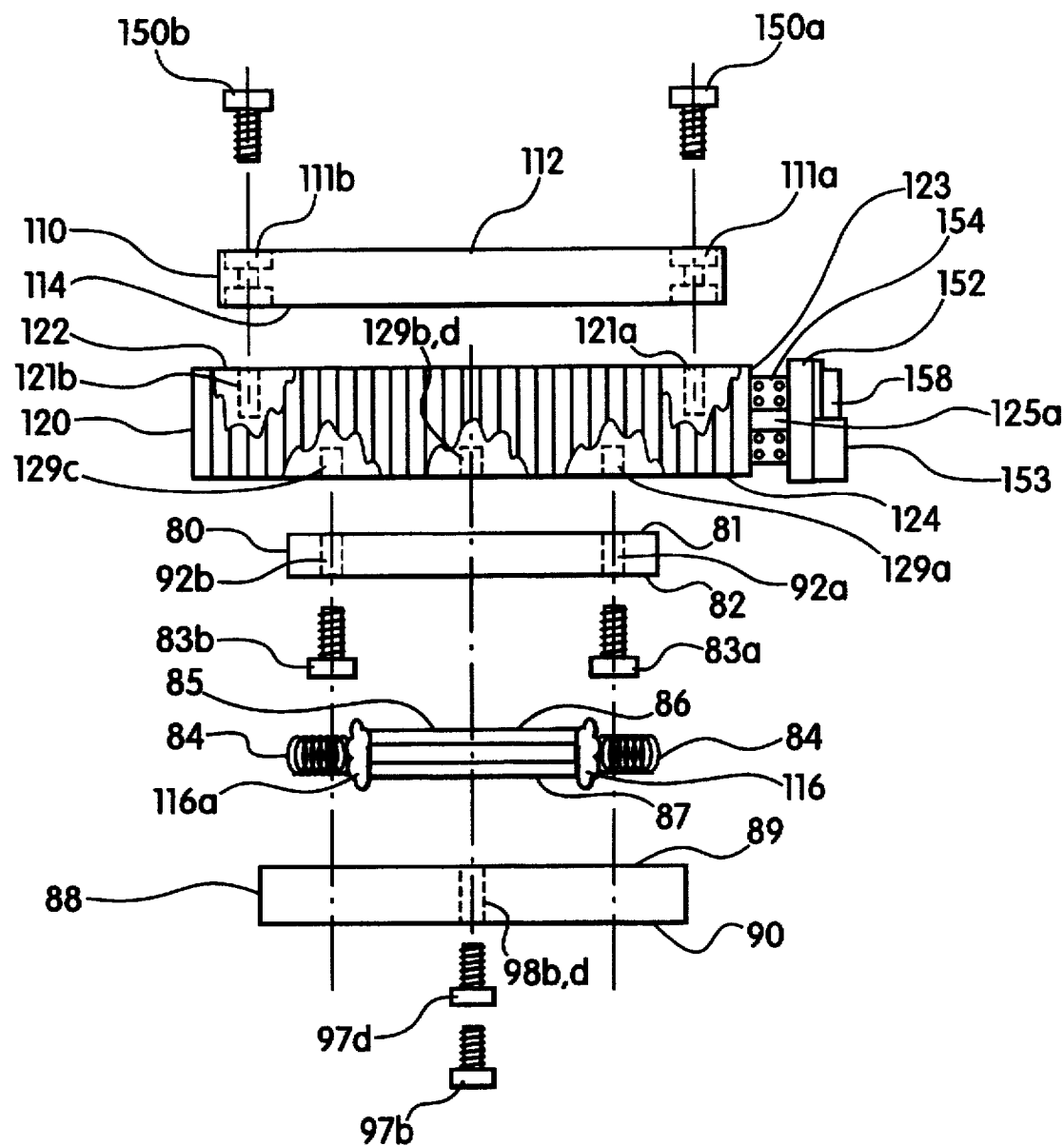
FIG. 6 shows an exploded view of components of the present invention, a thermoelectric assembly without the cover and cover plate.

FIG. 6 shows an exploded view of the thermoelectric assembly 75. The thermoelectric assembly 75 contains a Peltier device 85 which, when electric current is passed through the Peltier device 85 creates a temperature difference between a Peltier first surface 86 and a Peltier second surface 87. If the direction of the electric current through the Peltier device 85 is reversed, the temperature between the Peltier first surface 86 and Peltier second surface 87 is reversed.

Thus, in one mode of operation, Peltier second surface 87 becomes cooler than Peltier first surface 86; and in a second mode of operation where the direction of the electric current is reversed, Peltier first surface 86 becomes cooler than Peltier second surface 87. By attaching the radiator 120 with fan 110 to the first plate 80 which is affixed to the Peltier first surface 86, one maintains this Peltier first surface 86 at or close to ambient temperature. Peltier second surface 87 can then be either cooled or heated with respect to the ambient, depending on the direction of current flow to the Peltier device 85. For simplicity, operation of the device is described below for a cooling application of the peltier second surface 87 of the Peltier device 85. It is straightforward however, for those trained in the art, to understand the operation of the Peltier device 85 where the current is reversed to produce a heating effect of the Peltier second surface 87.

The thermoelectric assembly 75 consists of a fan 110 having a fan first surface 112 and a fan second surface 114. The fan second surface 114 is affixed to a heatsink, in this embodiment called a radiator 120, having a radiator first surface 122 and a radiator second surface 124. This embodiment utilizes radiator/fan module part# 979 L or Z 100AB121 manufactured by Wakefield Engineering of Wakefield, Mass. Between the radiator first surface 122 and the radiator second surface 124 are a plurality of fins 127, best seen in FIGS. 8 and 9. The radiator second surface 124 is affixed to a warm first surface 81 of a first plate 80. A warm second surface 82 of the first plate 80 is attached to the Peltier first surface 86 of a Peltier device 85. This embodiment utilizes Peltier device 85 Catalog# CP 1.4-71-10L manufactured by Melcor. Although this embodiment utilizes one Peltier device 85, multiple devices could be utilized (not shown), increasing the cooling or heating power of the thermoelectric assembly 75.

Figure 11:
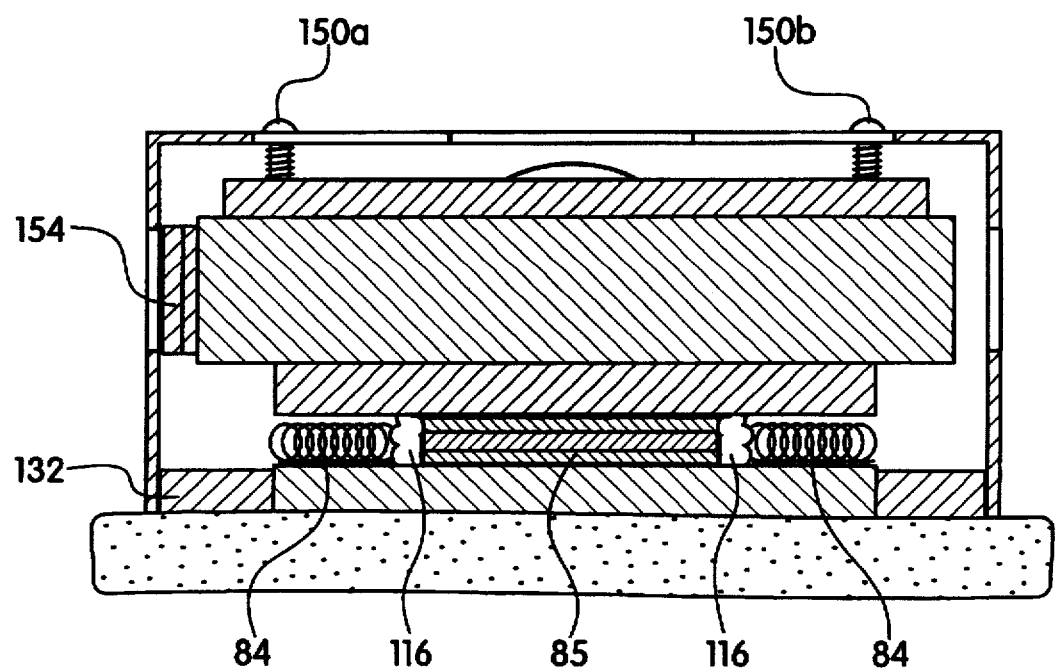
FIG. 11 shows a section view of the thermoelectric assembly along A—A in FIG. 10.

The Peltier second surface 87 of the Peltier device 85 is attached to a cool first surface 89 of a second plate 88. A cool second surface 90 of the second plate 88 is flush against a gel pack 95 in the installed position, as shown in FIG. 11. The first plate 80 and the second plate 88 are made from a material with a high thermal conductivity, in this embodiment copper.

FIGS. 6 & 11 shows a bead of a sealant 116 circumscribing Peltier device 85. Sealant 116 is used to prevent moisture from penetrating the Peltier device 85 and forms a watertight, pliable, non-conducting connection between the first plate 80, Peltier device 85 and second plate 88. One embodiment utilizes a silicone based sealant; other sealants may be used. The Peltier device 85 can be purchased pre-sealed which would eliminate the need to apply sealant 116.

First plate 80 and second plate 88 provide an effective way of transferring heat energy from the Peltier device 85 to the radiator 120 and the gel pack 95. As an additional benefit, first plate 80 and second plate 88 add significantly to the effective thermal mass of Peltier device 85 thereby decreasing potential damage to the Peltier device 85 from switching the device on or switching from a heating to a cooling mode or vice versa. An alternative embodiment could be built without the first plate 80 because the radiator 120 has a high thermal conductivity and thermal mass which can replace the function of the first plate 80.

An insulating material 84 is installed between the warm second surface 82 of first warm plate 80 and cool first surface 89 of the second plate 88. The insulating material circumscribes the Peltier device 85 to prevent heat transfer from the first plate 80 and the second plate 88. The insulating material 84 can be any high R-value material, in this embodiment open cell foam is used, but other insulating means could be utilized.

FIG. 6 also shows two of the four attachment means, a pair of cover screws 150a and 150b are shown. FIG. 10 shows a pair or cover screws 150c and 150d. Cover screws 150a, 150b, 150c and 150d are used to attach a cover 140 to the fan 110 and the radiator 120. The four cover screws 150a, 150b, 150c and 150d penetrate a plurality of cover holes 147a, 147b, 147c and 147d through a plurality of fan attachments 111a, 111b, 111c and 111d and engage a plurality of radiator attachments 121a, 121b, 121c and 121d thereby affixing the cover 140, fan 110 and radiator 120 together, FIGS. 9, 10, 11. For example, cover screw 150a penetrates cover hole 147a through fan attachment 111a and affixes in radiator attachment 121a. This embodiment shows four cover screws 150a, 150b, 150c and 150d, but more or less screws could be utilized.

The first plate 80 is attached to the radiator 120 by attachment means, in this embodiment, a pair of screws 83a and 83b. The screws 83a and 83b penetrate the first plate 80 through a pair of attachment holes 92a and 92c and attach to the radiator 120 second surface 124 in a pair of plate holes 129a and 129c, FIG. 6.

In like manner, attachment means, in this embodiment a pair of screws 97b and 97d are used to retain the Peltier device 85 between the first plate 80 and the second plate 88. Screws 97b and 97d penetrate the second plate 88 through a pair of attachment holes 98b and 98d and attach to the radiator 120 second surface 124 in a pair of plate holes 129b and 129d. The Peltier device 85 is centrally affixed between first plate 80 and second plate 88, FIG. 6. Screws 97b and 97d are made from a low thermal conductivity material such as nylon. Other embodiments of the screws 97b and 97d could be manufactured from other low thermal conductivity materials.

Second plate 88 has a temperature sensor or temperature measuring device, in this embodiment, a thermistor 104. In this embodiment, thermistor 104 is mounted on a thermistor edge 91 of second plate 88, FIG. 9. Other locations for the thermistor 104 could be utilized. The electrical resistance of the thermistor 104 is a strong function of the temperature of plate 88 and is part of a control circuit 152 which modulates the power applied to the Peltier device 85.

Figure 12A:
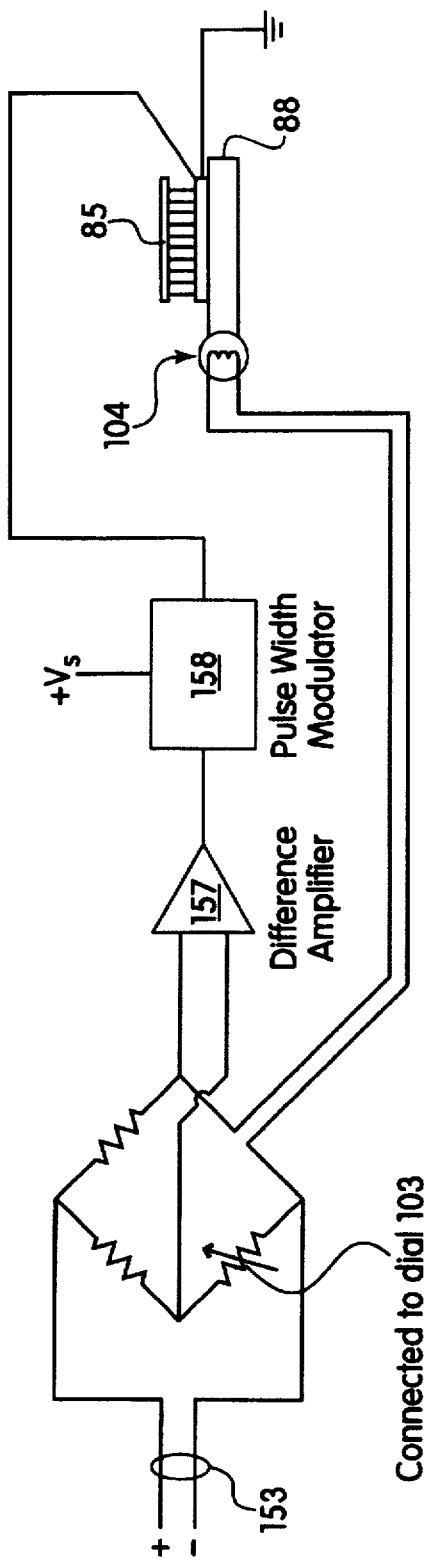
FIG. 12a shows a schematic view of one embodiment of the control circuit, including the Peltier device, and feed back provided by a temperature sensing device.

The control circuit 152, FIG. 12a, is schematically represented. The control circuit 152 consists of a bridge 156 which feeds a signal to a difference amplifier 157, in this embodiment an instrumentation amplifier, model AD504 manufactured by Analog Devices. One of the desirable features of instrumentation amplifiers is that in addition to providing amplification of the signal, they also have a high "common mode rejection". The output of amplifier 157 drives the input of a pulse width modulator 158, which in this embodiment is a Maxim Integrated Products model #MAX724. The pulse width modulator 158 then drives the Peltier device 85. Temperature feedback is provided by the thermistor 104 which is one arm of the bridge 156 and which is mounted on the thermistor edge 91 of plate 88.

The important feature about using a pulse width modulator 158 to control the Peltier device 85 is that pulse width modulator 158 drives the Peltier device 85 with a variable duty cycle square wave so that the control power semiconductor (not shown), inside the pulse width modulator 158 which drives the Peltier device 85 is either fully on or fully off. In this way, the power lost in the control power semiconductor (not shown) is minimized because the losses are a minimum when the device is switched completely on or off.

Typically, the pulse width modulator 158 operates at a switching frequency of 15 kHz. Typical operating efficiencies with the pulse width modulator are 85%. The bridge 156 serves to control the duty cycle which then determines the average power applied to the Peltier device 85. The balance point of the bridge 156 determines the temperature to which plate 88 is controlled. Hence the desired temperature can be adjusted with a temperature adjustment dial 103 which varies the resistance of one of the arms of the bridge 156.

Figure 4:
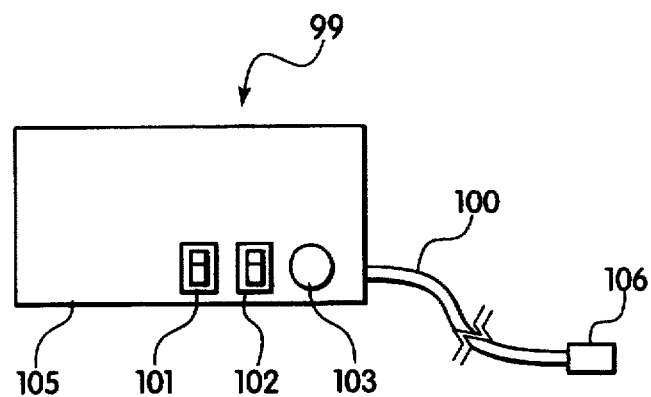
FIG. 4 shows a detail view of one of the components of the present invention, a portable power supply assembly, or battery pack.

The temperature adjustment dial 103 is shown in FIG. 4 located on a battery pack 99. Alternatively, power can be supplied through a 110 VAC household adapter 160 shown in FIG. 5 with a temperature adjustment dial 165 or a 12 VDC auto adapter 170 with a temperature adjustment dial 175. Alternative embodiments could have the temperature adjustment dials 103, 165 or 175 located on the cover 140 or other convenient location for easy access (not shown).

Figure 12B:
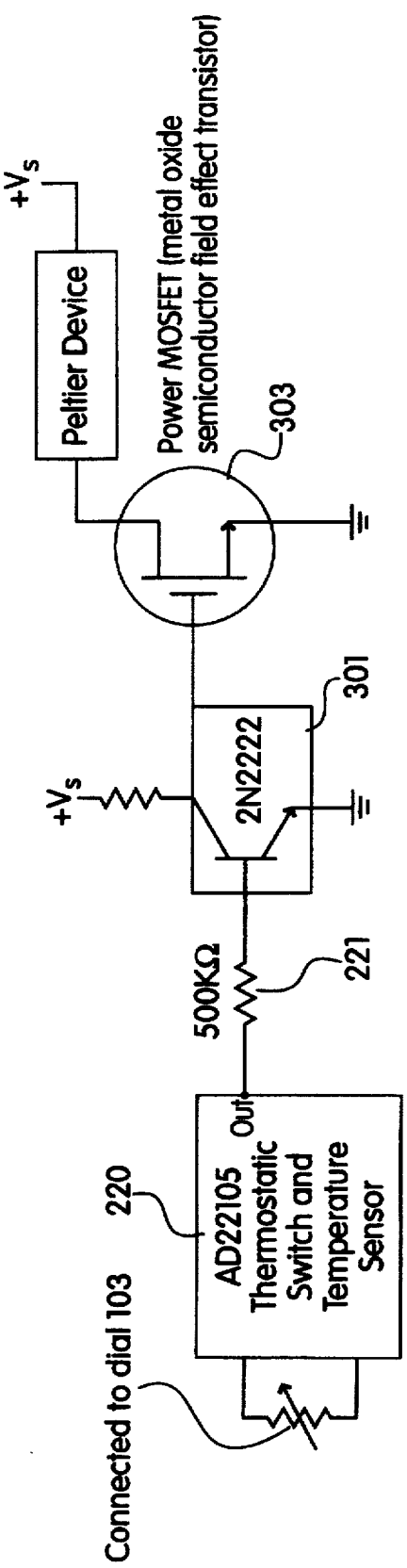
FIG. 12b shows an alternative embodiment of the control circuit, including the Peltier device, and feed back provided by a temperature sensing device.

As stated in the previous paragraph, the losses in the control circuit are about 15%, nevertheless it is still desirable to increase the efficiency of the controller further in order to maximize the duration the device can be operated with a portable battery pack 99. One alternate way to control the temperature is shown in the schematic of FIG. 12b. An integrated circuit 220, (IC), Analog Devices model 22105, is mounted on plate 88 in place of the thermistor 104. This IC 220 has a built in temperature sensor and a thermostatic switch with a hysteresis of approximately 4 degrees Centigrade. The temperature at which the switch operates is determined by a resistor connected between two of the IC's pins. The value of this resistor is controlled by temperature adjustment dial 103.

The "switch" operated by IC 220 controls a voltage at an output pin which is low when the temperature is too high and high when the temperature is too low. When the voltage is high (temperature too cold), the output is sufficient to turn on a transistor 301 connected to the output of IC 220, and hence the impedance of transistor 301 is small compared to a resistor 221. Thus, there is minimal voltage drop across transistor 301, which then is insufficient to turn on a MOS- FET power transistor 303 which drives the Peltier device 85. The opposite is true when the temperature is too hot. In this embodiment of the circuit, we have chosen transistor 301 to be a commonly available 2N2222 NPN transistor. There are many other transistors with similar characteristics which will work. A resistor 302 is a 10K ohm resistor and the MOSFET power transistor 303 is a IRFZ34 device or alternatively a MTP50N06EL device. As is well know to those trained in the art, there are many substitute parts which have equivalent electrical characteristics which can be used instead of those specifically mentioned for the control circuit 152.

The advantage of this alternate control circuit of FIG. 12b is that the losses of the circuit in FIG. 12a, which are caused by switching, are reduced because the switching occurs at a much lower rate. The MOSFET power transistor 303 is also turned either completely on or completely off similar to the pulse width modulator 158 power semiconductor and hence also has low power losses.

It is believed, based on this disclosure, that anyone skilled in the art could duplicate either of the control circuits described or utilize any of the many other control circuits which exist in the prior art for the purpose described here.

Figure 13:
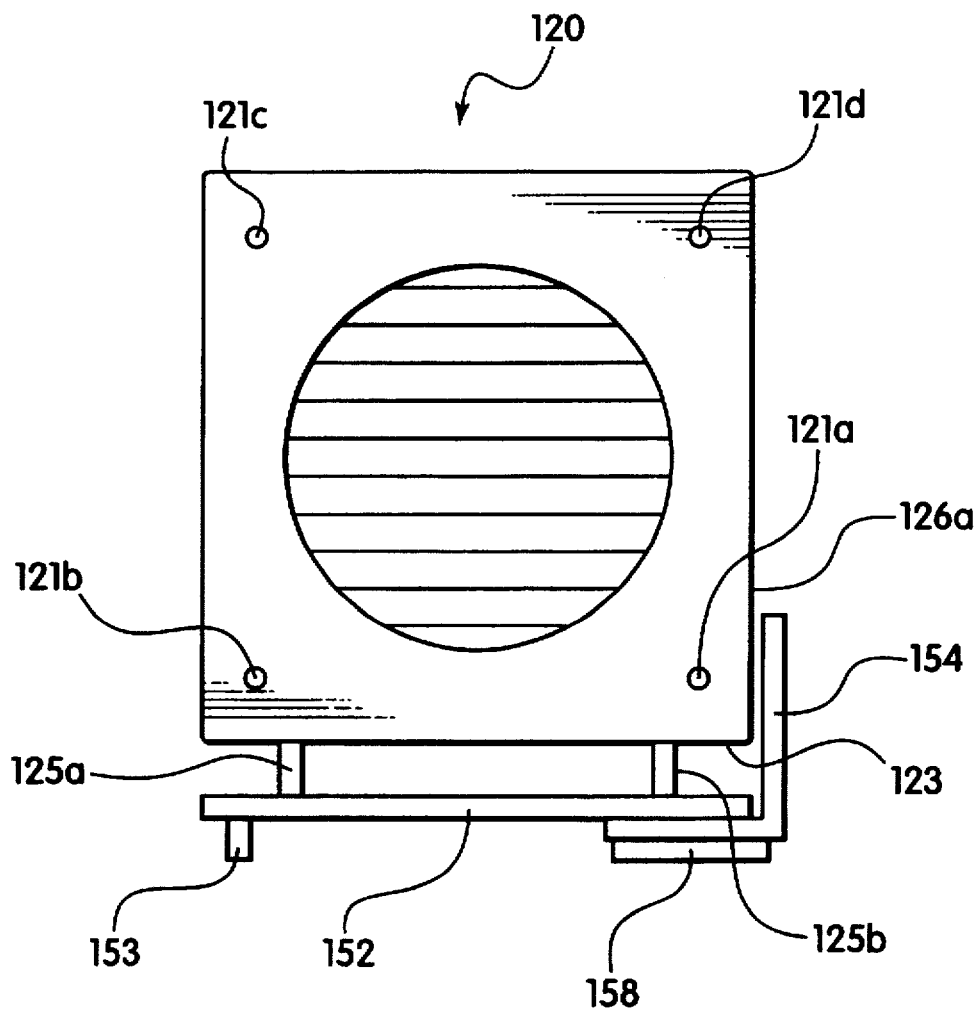
FIG. 13 Shows a top detail view of the radiator and control circuit assembly of the thermoelectric assembly.

The control circuit 152 is mounted to a radiator side plate 123 of radiator 120 on a plurality of standoffs 125a and 125b, in this embodiment two, FIG. 13. The pulse width modulator 158 of the control circuit 152 in FIG. 12a or the power MOSFET power transistor 303 of the circuit in FIG. 12b is located near the interface of radiator side plate 123 and a fin side 126a, FIG. 13. An L-shaped control heat sink 154 is attached to the pulse width modulator 158 and extends across finside 126a. The control heat sink 154 is cooled by the air flow exiting from fin side 126a, FIGS. 6, 9 and 13.

The power can be supplied by any number of standard power supplies such as a battery pack 99, FIG. 4. The battery pack 99 consists of a battery housing 105 containing batteries (not shown) with an on/off switch 101, a heat/cool switch 102 and the temperature adjustment dial 103 mounted to the battery housing 105. A wiring 100 connects the battery pack 99 to a power connector 153 of control circuit 152. The heat/cool switch 102 is used to switch the device from one that provides heat to a site to one that provides cooling to a site. The temperature adjustment dial 103, is used to adjust the temperature when the device is in the heating or cooling mode.

Figure 9:
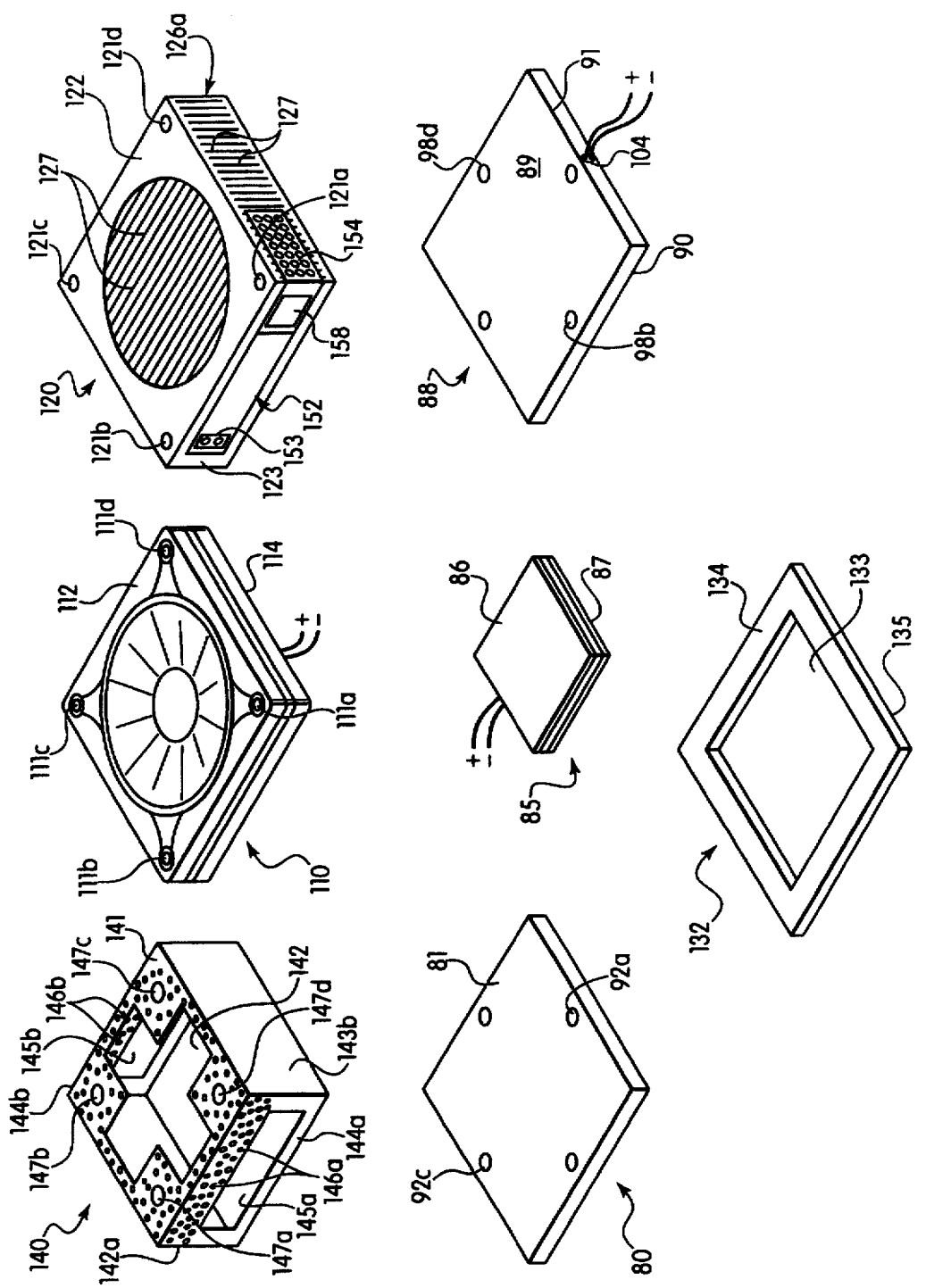
FIG. 9 shows a detailed view of the components of the thermoelectric assembly.
Figure 10:
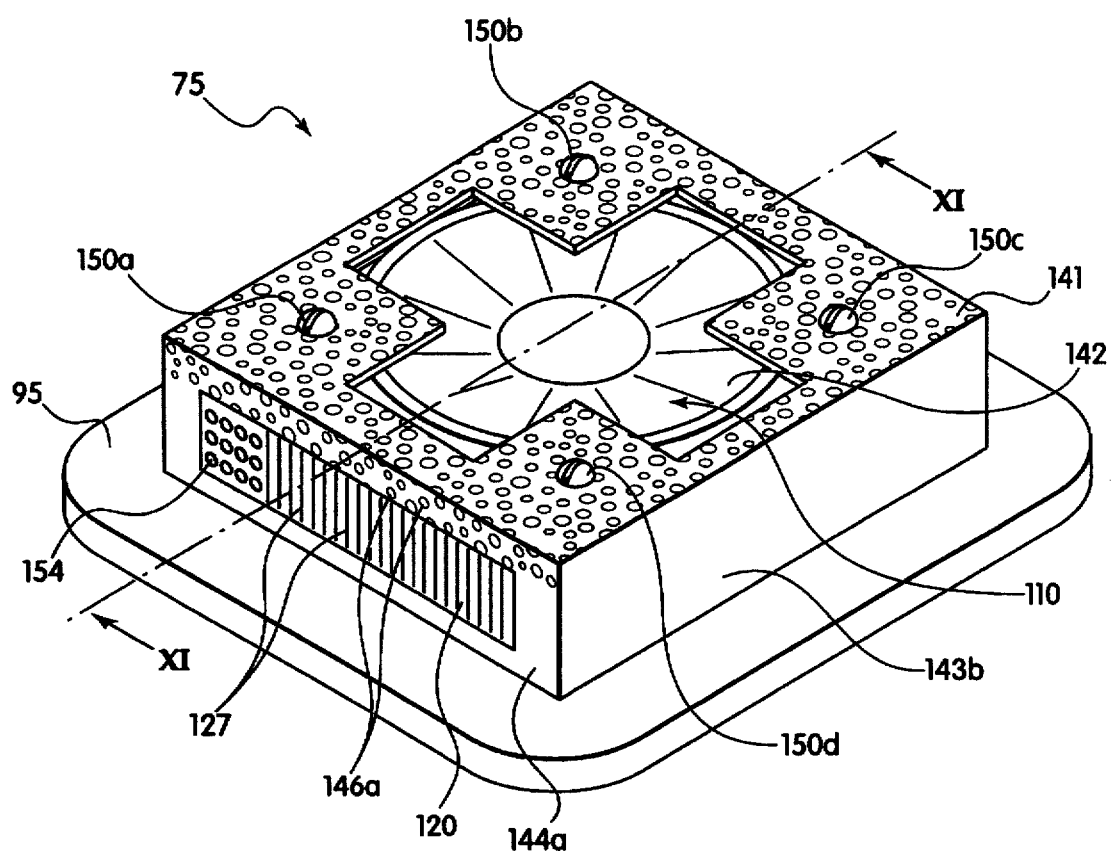
FIG. 10 shows an assembled view of one embodiment of the thermoelectric assembly.

FIG. 9 shows a cover plate 132, rectangular in shape with a plate void 133, and having a first side 134 and a second side 135. A cover plate 32 surrounds the second plate 88 in the installed position and mates with cover 140 to enclose the components of the thermoelectric assembly 75, best shown in sectional view A—A, FIG. 11.

Figure 8:
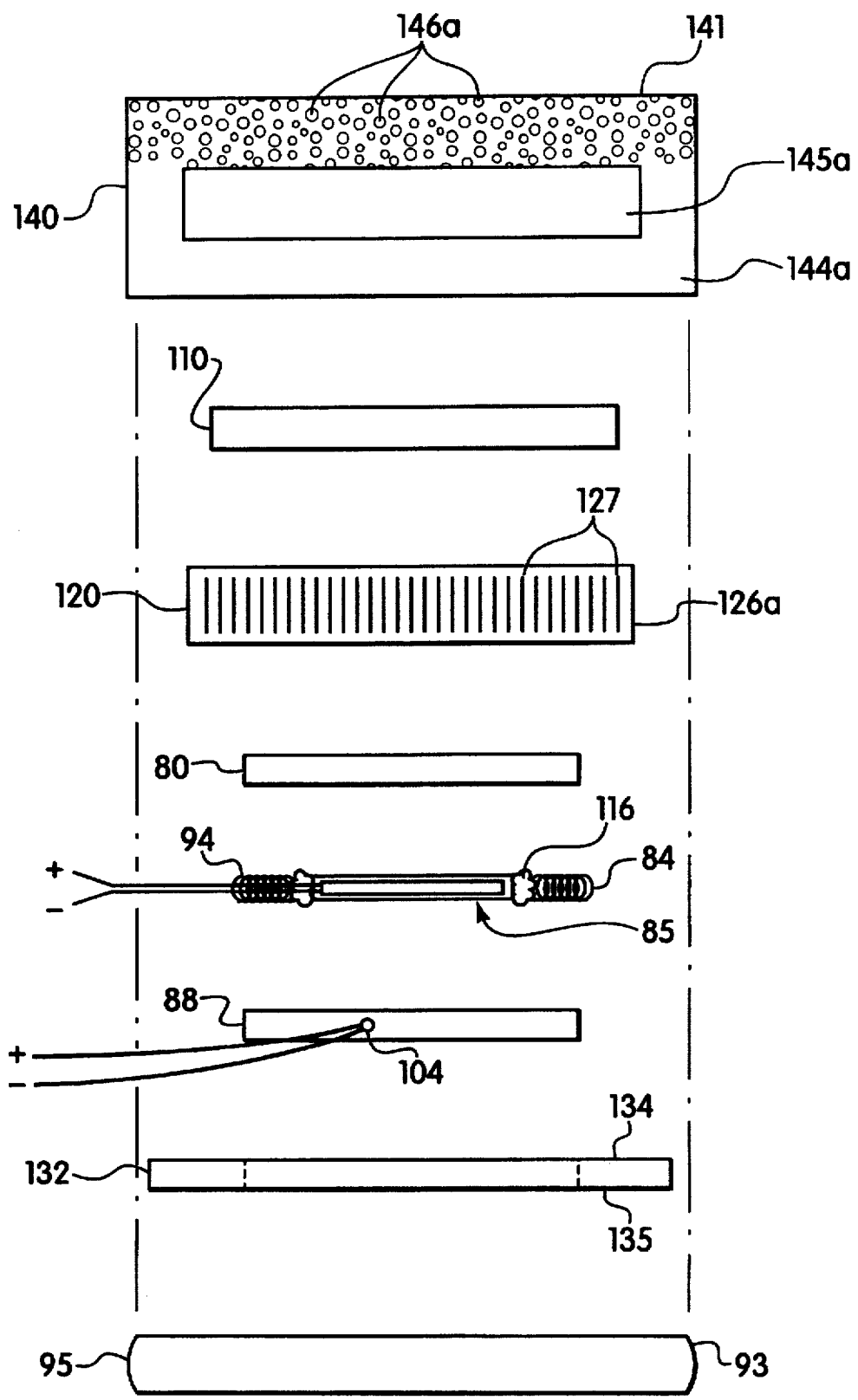
FIG. 8 shows an alternative exploded view of the thermoelectric assembly, cover, cover plate and gel pack.

FIG. 8, an exploded view of the thermoelectric assembly 75, includes the cover 140 and the cover plate 132. The cover 140 is a four sided container with a partial top, an intake surface 141, with a plurality of holes through to promote the flow of air to the fan 110 and an intake opening 142 centrally located in the intake surface 141, FIGS. 9 & 10. This embodiment shows, in FIGS. 9 & 10, intake opening 142 and a plurality of holes. It is to be understood that alternative designs of the intake opening 142 could be utilized such as a hole, slots, arced slots and others to provide for airflow. In addition, some embodiments may not need the holes in the intake surface 141 at all. A pair of closed sides 143a and 143b of the cover 140 are closed and a pair of open sides 144a and 144b of the cover 140 are open. A plurality of air vent holes 146a are shown through open side 144a in addition to a primary passage 145a. A plurality of air vent holes 146b are shown through open side 144b in addition to a primary passage 145b, FIG. 9.

In this embodiment, primary passages 145a and 145b are shown in FIG. 9 as rectangular in design having a plurality of vent holes 146a and 146b. Alternative designs could be utilized such as slots, circular openings or a series of square openings such that the vent holes 146a and 146b would not be necessary.

The primary passage 145a and vent holes 146a are open to allow airflow from the radiator 120 fin side 126a (FIG. 8) to ambient air. Primary passage 145b is open to allow airflow from a finside 126b of the radiator 120, FIG. 9, to ambient air.

When the fan 110 is energized, air is drawn through the intake surface 141 intake opening 142 through the fan 110 and into the radiator 120 through the first surface 122. In this embodiment, the air is dispersed in two directions and flows over the fins 127 to exit either finside 126a or finside 126b of the radiator 120, primary passages 145a and 145b and vent holes 146a and 146b. In alternative embodiments, the air exiting the radiator 120 could exit on more or less sides depending on the design of the radiator 120.

Figure 7:
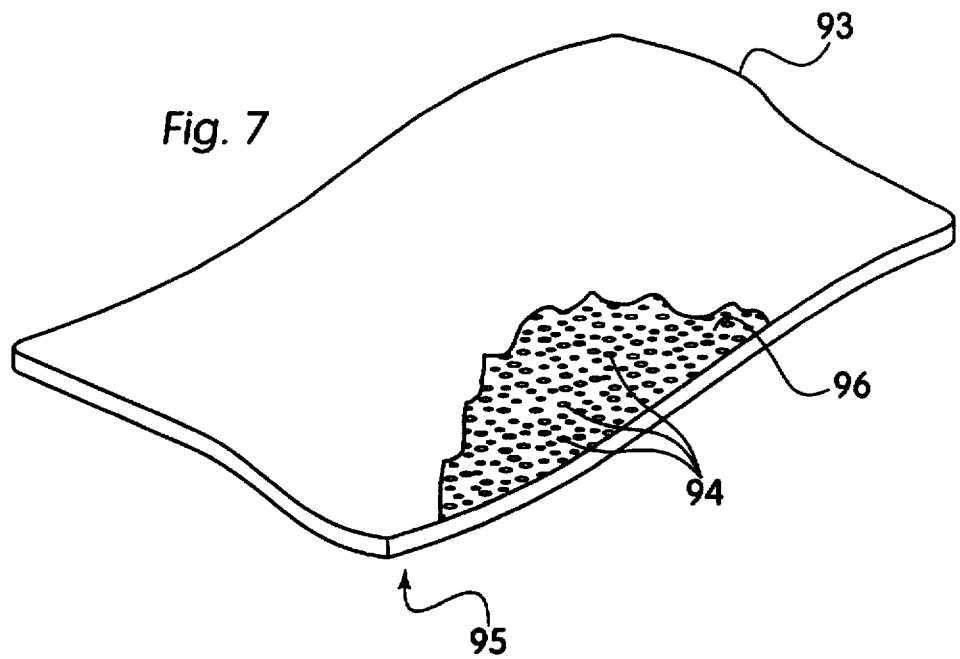
FIG. 7 shows a detail view of one of the components of the present invention, a gel pack.

FIG. 7 shows the gel pack 95. An outer casing 93 of the gel pack 95 is manufactured from a plastic material such that the gel pack 95 is relatively pliable at the operating temperatures and also hypo-allergenic. Contained within the gel pack 95 is a filler material 96. Filler material 96 is any readily available non-toxic materials well know in the prior art. This embodiment utilizes a filler material 96 with ammonium nitrate as its active ingredient. Other materials well known in the art may be substituted.

This embodiment utilizes a heat transfer material 94, made by SCM Metal Products, Inc. of Cleveland, Ohio Grade 150A. The heat transfer material 94 can be any material that has a relatively high thermal conductivity. This embodiment utilizes a copper based material that does not readily oxidize in the gel pack 95 material. The heat transfer material 94 can be in either a flake, granule or pellet form and is mixed and suspended with the filler material 96 contained within the gel pack 95. The concentration of the heat transfer material 94 in this embodiment is about 20% by weight.

To attach the injury pack holder 10 as shown in FIGS. 1 & 4, the user inserts (in this example a foot—not shown) a body part in the first end 15 through the unit and out the second end 16. The injury pack holder 10 is adjusted such that one of the module openings 55a, 55b or 55c is located over the injured area in which therapy is desired. In this example module opening 55a is located over the injured area.

Once the injury pack holder 10 is positioned correctly, the user inserts the thermoelectric assembly 75 with the gel pack 95 in contact with the second plate 88, into the module opening 55a. This stretches the retention mesh 60 such that the thermoelectric assembly 75 protrudes from the outer shell 22 and the gel pack 95 is in contact with the injured area. The user then inserts the battery pack 99 into, in this example, module 55c.

The battery pack 99 could also be placed into module 55b as a user may desire. Alternatively, the battery pack 99 could be affixed to the wearers belt or affixed to an article of clothing, or the body, in a waist bag or back pack, (not shown). A wiring connector 106, FIG. 4, is affixed to power connector 153, FIG. 12a, on the control circuit 152. On/off switch 101 is used and heat/cool switch 102 is used to choose either the heating or cooling mode. The temperature adjustment dial 103 is manually adjusted to the desired temperature.

Next the injury pack holder 10 is secured to the injured area. Attachment strap 70a is wrapped around the limb. Attachment strap 70a is inserted through strap loop 66a of strap attachment 65a, it is pulled over onto itself where hook and loop fasteners (not shown) affix the injury pack holder 10 securely to the body part.

In like manner, attachment strap 70b is threaded though strap loop 66b of strap attachment 65b and attachment strap 70c is threaded through strap loop 66c of strap attachment 65c. Both attachment straps 70b and 70c loop over onto themselves and are secured with hook and loop fasteners (not shown), FIGS. 1 and 3. Attachment straps 70a, 70b and 70c can be adjusted by disengaging the hook and loop fastening and tightening or loosening the attachment straps 70a, 70b and 70c to an adjustment that is comfortable for the user. The injury pack holder 10 can then be worn to perform normal daily activities.

Figure 5:
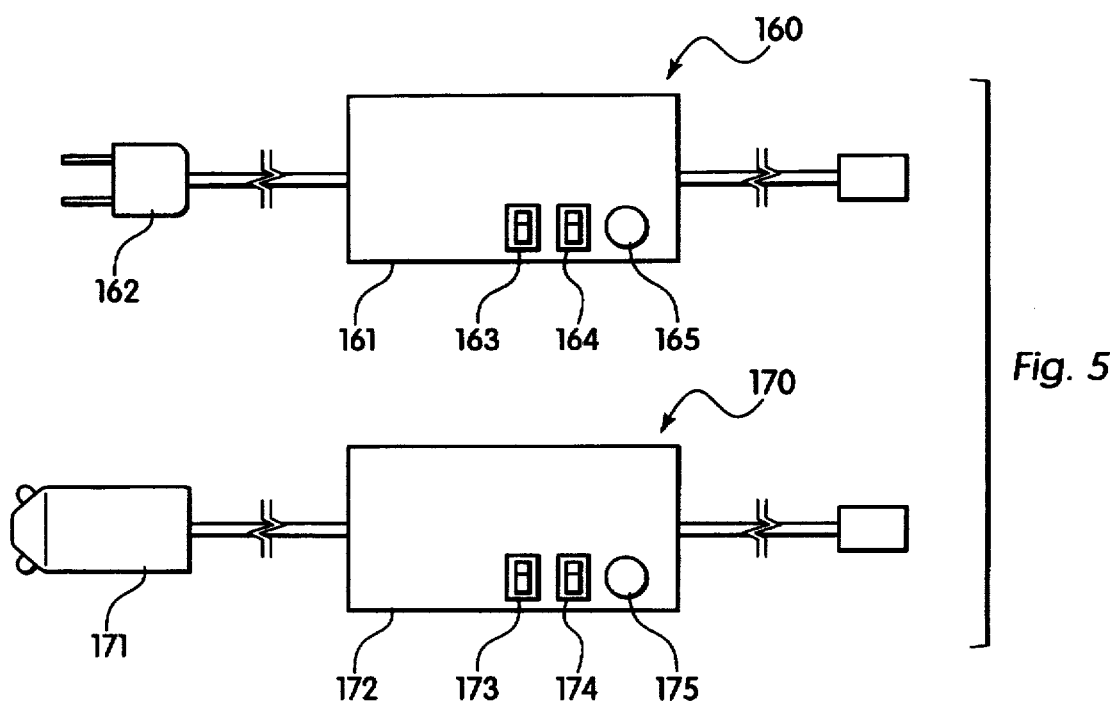
FIG. 5 shows alternative power supply adapters.

The thermoelectric assembly 75 may be powered by alternative power supplies such as household current, automobile power system, solar power or a combination of power sources. FIG. 5 shows alternative power supply adapters, a household adapter 160 and an auto adapter 170. The household adapter 160 has a power adapter 161 with a plug 162 for getting power from household current. Mounted on the power adapter 161, is an on/off switch 163, for turning the device on and off, and a heat/cool switch 164. A temperature adjustment dial 165 is used to adjust the temperature of the device to a user defined temperature. A wiring connector 166 plugs into the power connector 153 on control circuit 152, FIGS. 6, 13.

In a similar manner, an auto adapter 170, can be used to power the thermoelectric assembly 75 when it is utilized in an automobile. The auto adapter 170 has a lighter plug 171 and a switch housing 172. The switch housing 172 has an on/off switch 173, a heat cool switch 174 and a temperature adjustment dial 175. A wiring connector 176 of auto adapter 170 plugs into the power connector 153 on control circuit 152.

These adapters thereby allow the use of the injury pack holder 10 in the home or anywhere household current is available, in the car provided a cigarette lighter or other power supply is available, or when a user is away from either of the above by use of the battery pack 99.

Figure 14A:
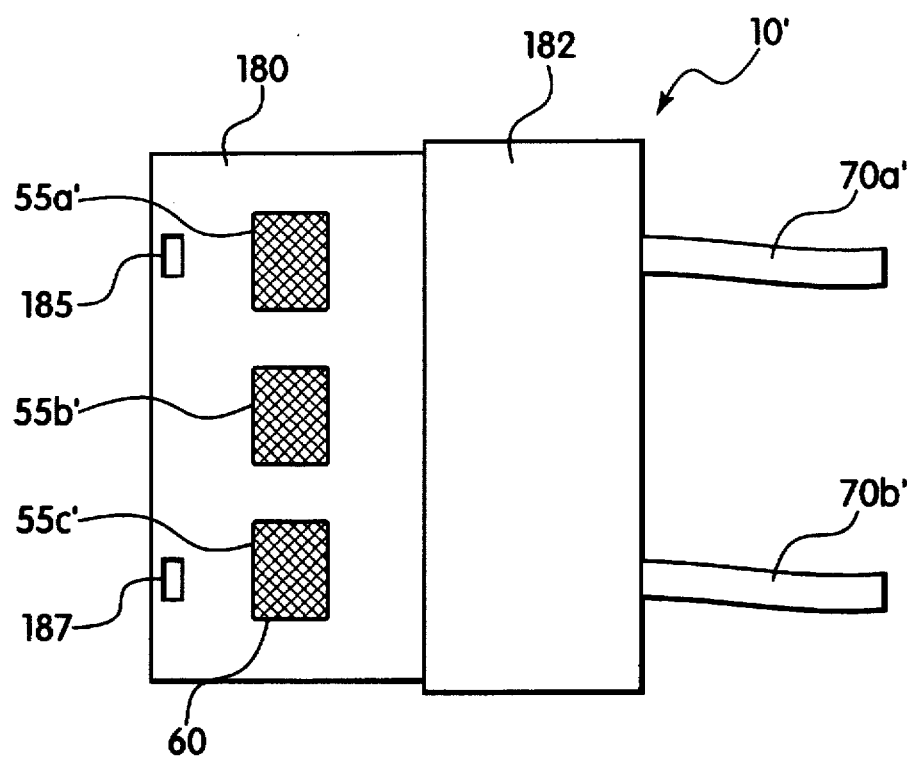
FIGS. 14A and 14B show alternative embodiments of the injury pack holder.
Figure 14B:
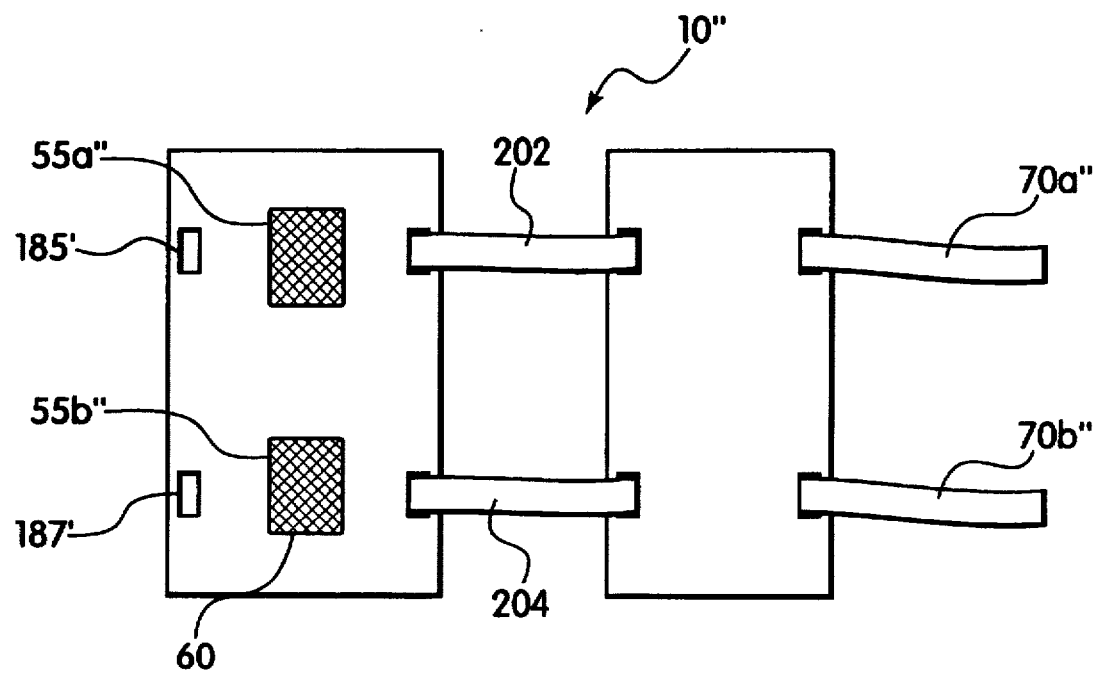

FIGS. 14A & B shows alternative embodiments of the injury pack holder 10' and 10". Injury pack holder 10' has a rigid holder 180 with a plurality of module openings 55a', 55b' and 55c', other embodiments could utilize more or fewer module openings. Mesh 60 covers the module openings as shown and discussed with reference to FIG. 1. In like manner as injury pack holder 10, the thermoelectric assembly 75 (not shown) is placed in one of the module openings to provide heat or cooling to the body part. The rigid holder 180 is rigid so that the injury pack holder 10' may be utilized to rigidly hold the body part in the event of a break or potential break to a body part. This embodiment could be utilized by emergency or rescue personnel. A flexible shell 182 is affixed to one edge of the rigid holder 180 and on an opposite edge has a plurality of attachment straps, 70a', 70b', in this embodiment two. The attachment straps 70a' and 70b' wrap around the limb or body part. Attachment strap 70a' is inserted in a strap slot 185, likewise attachment strap 70b' is inserted in a strap slot 187. The attachment straps 70a' and 70b' are folded back onto themselves and affix by an attachment means, in this embodiment hook and loop fasteners, (not shown).

Likewise injury pack holder 10" has a rigid holder 180' attached to a rigid back plate 200 by in this embodiment, a connection strap 202 and a connection strap 204. A pair of attachment straps 70a" and 70b" are inserted through a pair of strap slots 185' and 187'. The strap slots 185' and 187' are, as in above, folded over onto themselves and affixed by attachment means, in this embodiment hook and loop fasteners. Because this embodiment utilizes two rigid portions, rigid holder 180 and rigid back plate 200, this provides even more support to a potentially broken limb. This embodiment shows a pair of module openings 55a" and 55b", obviously more or fewer module openings could be utilized. The module openings 55a" and 55b" have retention mesh 60 to provide retention of the thermoelectric assembly 75. The thermoelectric assembly 75 provides heating or cooling to a particular area depending on a users needs, as previously discussed.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. A modular heating and cooling device comprising:

mounting means for mounting a thermoelectric assembly, said mounting means having an outer shell with at least one module opening, said outer shell being flexible radially and substantially rigid longitudinally, an attachment means for attaching the mounting means to a body part, said attachment means adjustable to provide adjustable variable compressive force to the body part; and the thermoelectric assembly having at least one Peltier device with a radiator on one side and a second plate on an opposite side of said Peltier device, said radiator adjacent a fan for promoting air flow through said radiator, a control circuit affixed to said radiator controlling said Peltier device, a temperature sensor attached to said second plate for providing feedback to said control circuit which controls a power supply for supplying power to said thermoelectric assembly.

2. The modular heating and cooling device of claim 1 wherein:

said second plate is made from a high thermal conductivity material.

3. The modular heating and cooling device of claim 1 further including:

a five sided cover and a mating cover plate for encasing said thermoelectric assembly.

4. A heating and cooling device comprising:

a thermoelectric assembly comprising at least one Peltier device and a first plate attached to a Peltier warm surface and a second plate attached to a Peltier cool surface, said first plate and said second plate insulated from one another by insulating means for insulating and discouraging heat transfer between said first plate and said second plate, a radiator affixed to said first plate on a first surface, said radiator having a fan in close proximity for providing air flow and encouraging the transfer of heat energy from said radiator to ambient air, a control circuit for controlling said Peltier device, feedback means for reporting feedback signals to said control circuit for adjusting said Peltier device;

a gel pack for attachment to said second plate, said gel pack having a flexible shape and containing a filler material mixed with a high thermal conductivity heat transfer material, said heat transfer material for increasing the speed of heat transfer from said second plate through said gel pack; and a power supply for providing electrical power to said thermoelectric assembly.

5. The heating and cooling device as recited in claim 4 wherein:

said second plate and said first plate are manufactured from a high thermal conductivity material such as copper.

6. The heating and cooling device as recited in claim 4 wherein:

said heat transfer material is in the form of flakes or pellets and is relatively inert in said filler material.

7. The heating and cooling device as recited in claim 4 further comprising:

a five sided cover and a mating cover plate for enclosing said thermoelectric assembly.

8. A modular cooling and heating device comprising:

a thermoelectric assembly having a Peltier device with a warm surface and a cool surface, a first plate having a second surface affixed to said warm surface to encourage heat transfer, a radiator affixed to said first plate first surface, a fan attached to said radiator for encouraging heat transfer from said radiator to ambient air, a second plate having a first surface affixed to said Peltier device cool surface to encourage heat transfer, a gel pack containing a viscous filler material and a high thermal conductivity heat transfer material, said gel pack adjacent said second plate for enhancing the transfer of heat energy from said second plate, a control circuit attached to said radiator and interconnected to said Peltier device, fan, and a feedback means, said feedback means for providing feedback to said control circuit;

a holder having at least one module opening for containing said thermoelectric assembly in a fixed position; and power means for supplying power to said thermoelectric assembly.

9. The modular cooling and heating device as defined in claim 8 wherein:

said high thermal conductivity heat transfer material is in the form of flakes or pellets and said heat transfer material is not degraded by said filler material.

10. The modular cooling and heating device as defined in claim 8 further comprising:

a five sided cover and a mating cover plate each having air flow means for allowing air flow, said cover and said plate encasing the thermoelectric assembly.

* * * * *